United States Patent [19]
Ohta

[11] Patent Number: 5,173,788
[45] Date of Patent: Dec. 22, 1992

[54] IMAGE READING DEVICE HAVING MOIRE DEPRESSING UNIT

[75] Inventor: Yuichi Ohta, Anjo, Japan

[73] Assignee: Brother Kogyo Kabushiki Kaisha, Nagoya, Japan

[21] Appl. No.: 651,009

[22] Filed: Feb. 5, 1991

[30] Foreign Application Priority Data

Feb. 7, 1990 [JP] Japan .................................. 2-28048
Jun. 27, 1990 [JP] Japan .................................. 2-169429
Aug. 24, 1990 [JP] Japan .................................. 2-223580

[51] Int. Cl.$^5$ ............................................. H04N 1/415
[52] U.S. Cl. ...................................... 358/454; 358/426; 382/43
[58] Field of Search ............... 358/452, 453, 454, 426, 358/133; 382/27, 31, 43, 45

[56] References Cited

U.S. PATENT DOCUMENTS 5,051,840 9/1991 Watanabe et al. .................. 358/426
5,109,451 4/1992 Aono et al. ............................ 382/43

Primary Examiner—Edward L. Coles, Sr.
Assistant Examiner—Kim Y. Vu
Attorney, Agent, or Firm—Oliff & Berridge

[57] ABSTRACT

In an image reading device for reading an original image, an original image is picked up and converted into two-dimensional positional image data represented in a two-dimensional positional coordinate system. The two-dimensional positional image data is further converted into two-dimensional spatial frequency image data represented in a two-dimensional spatial frequency coordinate system, and then into high frequency image data and low frequency image data. The high frequency image data is subjected to moire component selecting and depressing operations to correct the high frequency image data whose moire components are depressed, and then the low frequency image data and the corrected high frequency image data are reconverted into corrected two-dimensional positional image data, thereby reproducing the original image with no moire.

11 Claims, 8 Drawing Sheets

IMAGE READING DEVICE HAVING MOIRE DEPRESSING UNIT

BACKGROUND OF THE INVENTION

This invention relates to an image reading device, and more particularly to an image reading device having a moire depressing unit for depressing occurrence of moire of an image to be read.

A line image sensor comprising plural photoelectric transducers such as charge-coupled devices has been generally utilized as an image reading device for reading an original image in a fax machine, a digital copying machine or the like. When an original image to be printed with dots is read by this type of image reading device, an output signal is frequently provided with moire, which does not exist in the original image. It has been known that the moire occurs in a case where an original image is dot-printed, and a pitch interval of dots is near to a sampling pitch of an image sensor for reading the original image. In order to depress the moire, there has been conventionally utilized an optical low path filter through which signals of frequency components homogeneously contributing to the moire are eliminated. In such a low path filter, since all signals are homogeneously smoothed, signals of high frequency components are also eliminated by the low path filter even though they are parts of the image components and do not contribute to the moire. As a result, edge portions of the original image are blurred and this resolution of the image is reduced.

SUMMARY OF THE INVENTION

An object of this invention is to provide an image reading device capable of reading an original image without reducing resolution of the image and losing an image quality, and reproducing the original image with no moire.

In order to attain the above object, an image reading device according to this invention comprises image pickup means for optically picking up the original image and electrically converting into two-dimensional positional image data represented in a two-dismensional positional coordinate system, transforming means for converting the two dimensional positional image data into two-dimensional spatial frequency image data represented in a two-dimensional spatial frequency coordinate system, separating means for separating the two-dimensional spatial frequency image data into high frequency image data and low frequency image data, image data correcting means for depressing moire components of the high frequency image data to correct the high frequency image data, composite means for combining the low frequency image data and the corrected high frequency image data to thereby obtain the corrected two-dimensional frequency image data, retransforming means for reconverting the corrected two-dimensional frequency image data into corrected two-dimensional positional image data, and outputting means for outputting the corrected two-dimensional positional image data to reproduce the original image with depressing moire.

According to the image reading device of this invention, the original image signal represented in the two-dimensional discrete positional coordinate system is converted into an image signal represented in a non-positional discrete coordinate system such as a two-dimensional discrete correlative coordinate system to extract the image signal contributing to the moire and depress the moire components with the threshold levels, and then the corrected image data is reconverted into the corrected image data represented in the two-dimensional discrete positional coordinate system to reproduce the original image having no moire.

DETAILED DESCRIPTION OF THE INVENTION

Preferred embodiments according to this invention will be described hereunder with reference to the accompanying drawings.

Figure 1:
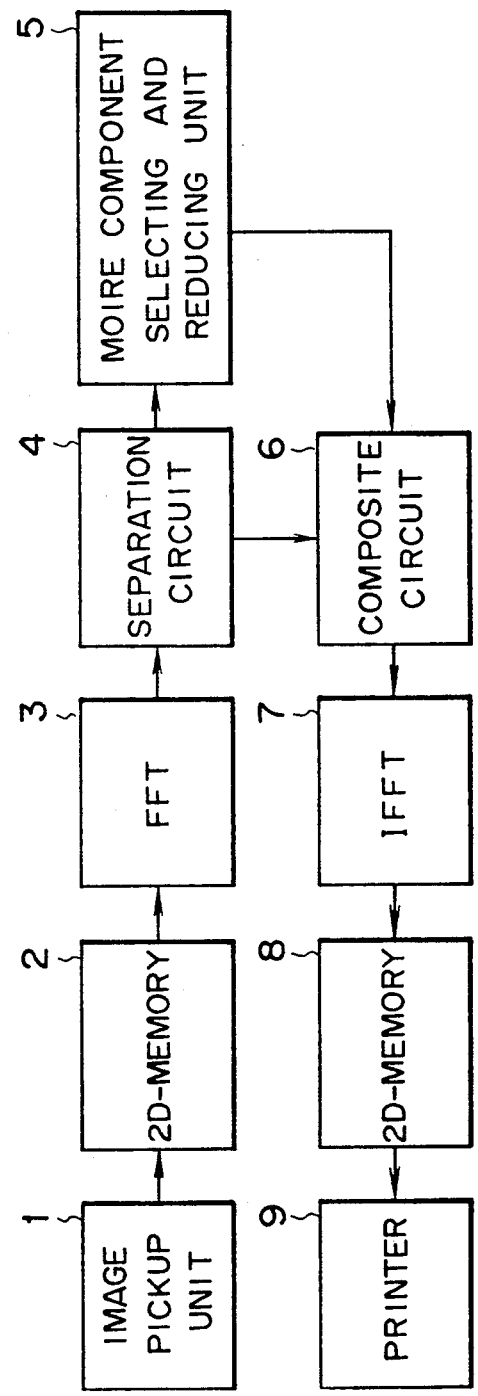
FIG. 1 is a block diagram for showing a first embodiment of the image reading device according to this invention.

FIG. 1 is a block diagram for showing a first embodiment of the image reading device according to this invention.

The first embodiment of the image reading device includes an image pickup unit 1 such as an image sensor for reading an original image to output image signals, a two-dimensional memory 2 for storing the image signals outputted from the image pickup unit 1 as image information represented in a two-dimensional discrete positional coordinate system (hereinafter referred to as "discrete positional image data"), a transforming unit 3 such as a fast Fourier transformer (FFT) for conducting a fast Fourier transform on the discrete positional image data stored in the memory 2 to convert the discrete positional image data into another type image information represented in a two-dimensional discrete spatial frequency coordinate system (hereinafter referred to as "discrete spatial frequency image data"), a separation (or frequency separation) circuit 4 for separating high and low frequency components of the discrete spatial frequency image data from each other before eliminating moire components from the discrete spatial frequency image data as described later, a moire component selecting and depressing unit 5 for selecting and depressing moire components from the high frequency components to thereby perform an image data correcting process (that is, moire component selecting and depressing processes), a composite (frequency composite) circuit 6 for combining the low frequency components and the high frequency components which have been subjected to the moire component selecting and depressing process in the composite circuit 6 and outputting the combined components as corrected frequency image data, a retransforming unit 7 such as inverse Fourier transformer (IFFT) for conducting a fast inverse-Fourier transform on the corrected frequency image data of the composite circuit 6 to reconvert the corrected frequency image data into corrected positional image data in the two-dimensional discrete positional coordinate system, a two-dimensional memory 8 for storing the corrected positional image data of the retransforming unit 7, and an output unit such as a printer 9 for outputting the corrected positional image data memorized in the memory 8, for example, for a printing operation. In the image reading device thus constructed, the moire component selecting and depressing unit 5 may comprise two separated units such as a moire component selecting unit for selecting (or extracting) positional coordinate values of the moire components from all of the high frequency components and a moire component depressing unit for performing a correcting operation of the high frequency image data, as described later. Further, the memories 2 and 8 may be identical to each other.

Figure 2:
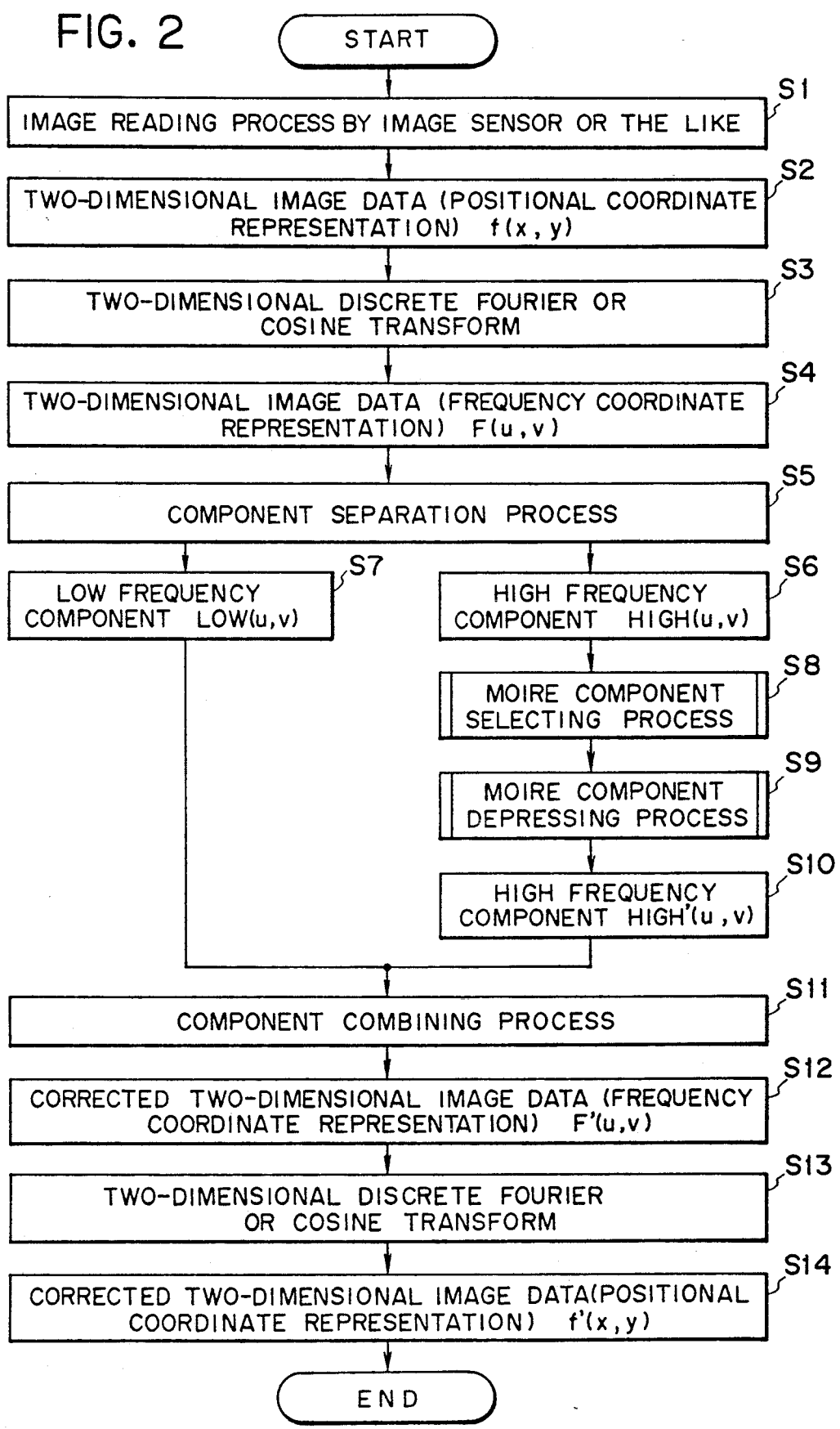
FIG. 2 is a flow chart for showing an image data correcting process of the image reading device as shown in FIG. 1.

FIG. 2 is a flow chart for showing the image data correcting process according to this embodiment.

First, an original image is picked up by the image pickup unit 1 such an image sensor or the like to perform an image input operation (step S1). The input original image signal is stored in the memory 2 as two-dimensional positional image data (x,y). The two-dimensional positional image data in the memory 2 corresponds to an electrical representation of light-and-shade distribution of the original image in the two-dimensional coordinate system (X and Y plane), and each signal value of the image data at each positional coordinate (x,y) is represented by f(x,y) (step S2). Next, the two-dimensional positional image data is subjected to the two-dimensional discrete Fourier transform (or two-dimensional discrete cosine transform) in the FFT 3 to thereby convert the positional image data represented in the positional coordinate system into corresponding frequency image data represented in the spatial frequency coordinate system (step S3). That is, in a step S4, a two-dimensional positional image data f(x,y) which is a function of a positional coordinate value (x,y) is converted into a two-dimensional frequency image data F(u,v) which is a function of a frequency coordinate value (u,v).

In the separation circuit 4, the frequency image data obtained in the step S3 are filtered to separate low frequency components from high frequency components (step S5). For example, in a case where the maximum values of the positional coordinate values (x,y) are 256 and 256, respectively, the low frequency components whose frequency range satisfies the following inequality are separated by a suitable filtering process.

$$-60 < u < 60 \text{ and } -60 < v < 60$$

The low frequency components LOW(u,v) separated in the step S5 are directly subjected to a combining process (step S11) and then used as low frequency components of a corrected two-dimensional frequency image data (S12). On the other hand, the high frequency components separated in the step S5 are subjected to a moire component selecting process (S8) to extract suitable frequency coordinate values (u,v) whose frequency image data HIGH(u,v) satisfy a predetermined condition as described later, and then the extracted frequency components HIGH(u,v) are subjected to a moire component depressing process (S9) to correct the high frequency image data and obtain the corrected high frequency image data HIGH'(u,v).

The low frequency image data LOW(u,v) and the corrected high frequency image data HIGH'(u,v) are combined with each other to obtain the corrected frequency image data F'(u,v) (step S12). The corrected frequency image data F'(u,v) are subjected to the inverse Fourier transform in the IFFT 7 so as to be converted into the two-dimensional corrected positional image data f'(x,y) whose moire is depressed (S14). The two-dimensional positional image data thus obtained are stored in the memory 8 and then outputted to the printer 9 or the like.

Figure 3:
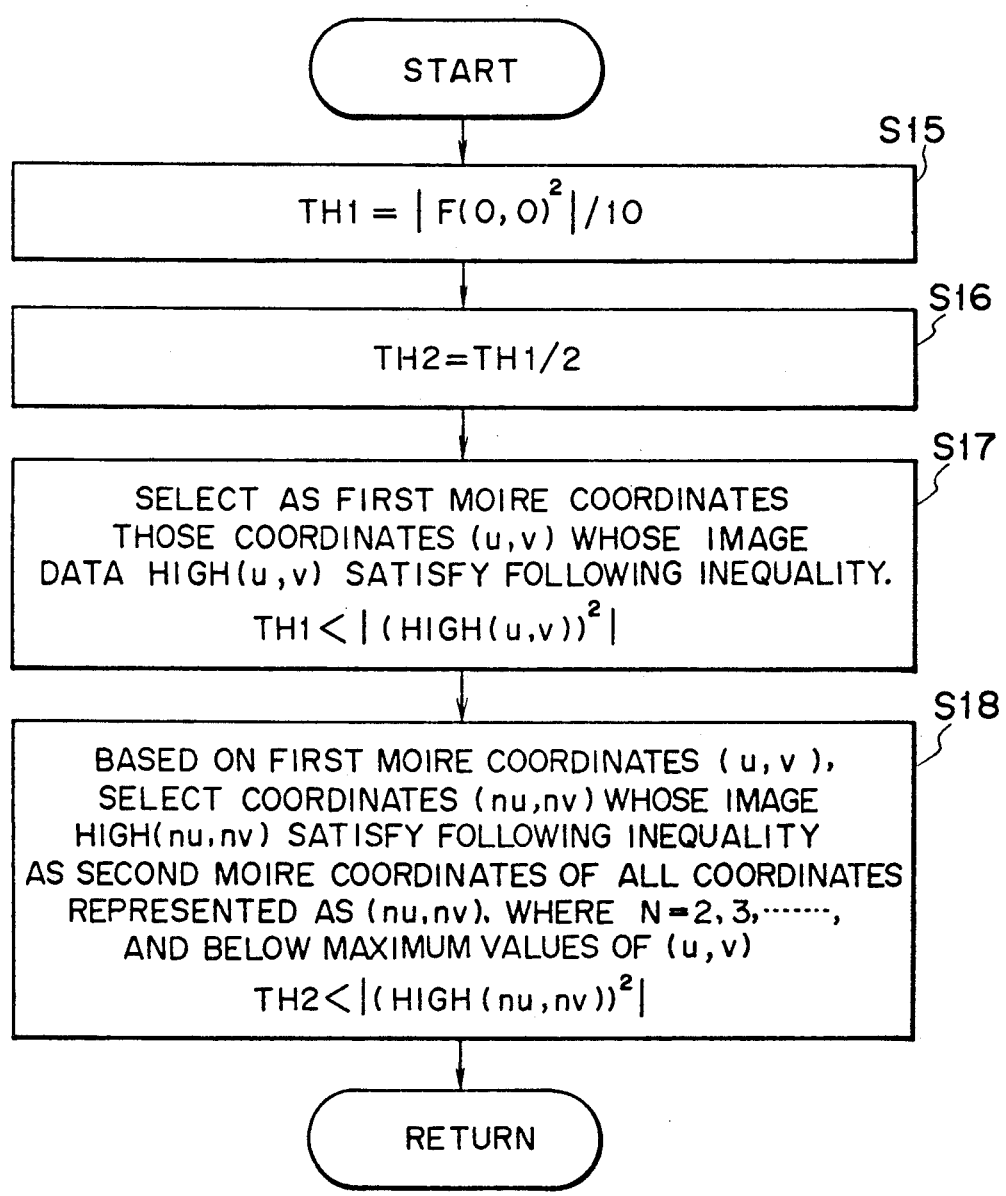
FIG. 3 is a flow chart for showing a moire component selecting process of the first embodiment.

FIG. 3 is a flow chart for the moire component selecting process in the step S8.

The moire component selecting process is carried out by comparing each of the high frequency components with two predetermined threshold levels TH1 and TH2. The first threshold level TH1 is set to one-tenth of an absolute value of $F(0,0)^2$ by rule of thumb (step S15), and the second threshold level TH2 is set to the half of the first threshold level TH1 (step S16). The absolute value of the second power of each high frequency image data HIGH(u,v), that is, $|HIGH(u,v)^2|$ is compared with the first threshold level TH1, and a first group of frequency coordinate values (u,v) whose high frequency image data HIGH(u,v) satisfy the following inequality, are selected as a first moire group of frequency coordinate values m1(u,v) for the moire components (S17).

$$TH1 < |(HIGH(u,v))^2|$$

Subsequently, a second moire group of frequency coordinate values m2(u,v) for the moire components are selected on the basis of the frequency coordinate values m1(u,v) of the first moire group (step S18) by the following process.

First, on the basis of the first frequency coordinate values m1(u,v) of the first moire group, n-fold frequency coordinate values (nu,nv) each of which has two components nu and nv obtained by multiplying m1(n,v) with n are beforehand selected, where n is an integer. Thereafter, the absolute value of the second power of each HIGH(nu,nv), that is, $|HIGH(nu,nv)^2|$ is compared with the second threshold level TH2, and a group of frequency coordinate values (nu,nv) whose high frequency image data HIGH(nu,nv) satisfy the following inequality are selected as a second moire group of frequency coordinate values m2(u,v) for the moire components.

$$TH2 < |(HIGH(nu,nv))^2|$$

In the above steps, the first moire coordinates m1(u,v) and the first moire components thereof HIGHm1(u,v) and the second moire coordinates m2(u,v) and the second moire components HIGHm2(u,v) thereof are finally obtained.

Figure 4:
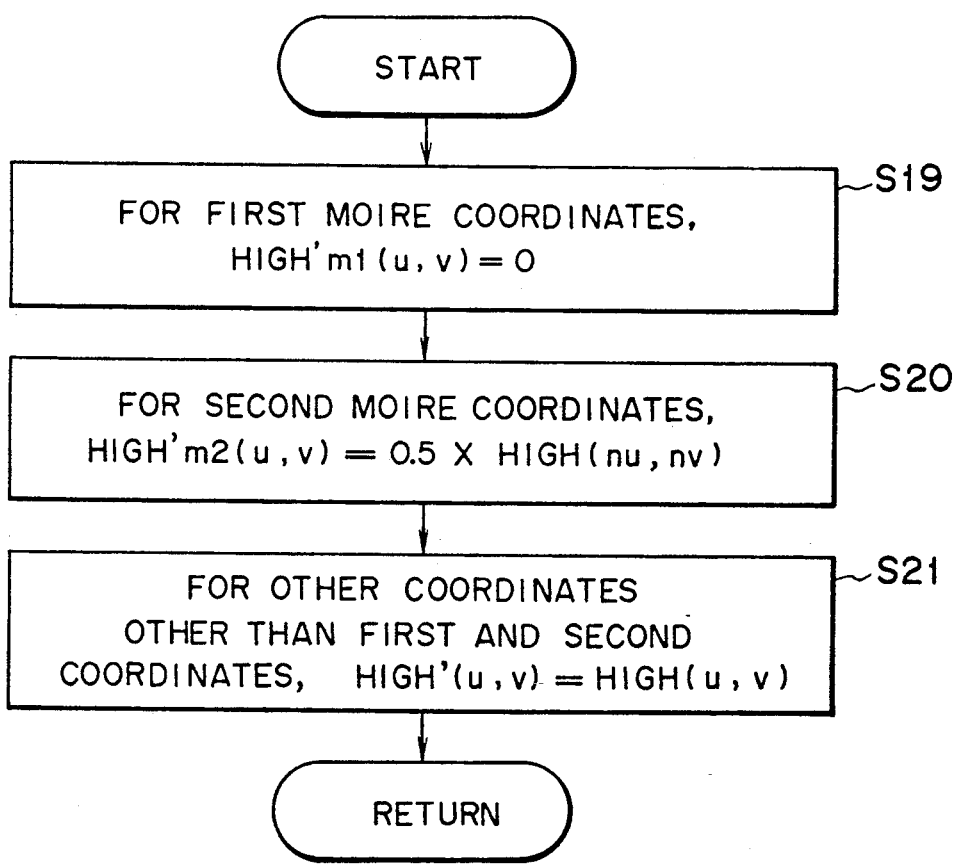
FIG. 4 is a flow chart for showing a moire component depressing process of the first embodiment.

FIG. 4 is a flow chart for the moire depressing process for the selected moire components.

In this embodiment, all signal values of the frequency image data HIGHm1(u,v) of the first moire group are set to zero to obtain a part of the corrected frequency image data HIGH'm1(u,v)=0 (step S19), while all signal values of the frequency image data HIGHm2(u,v) of the second moire group are multiplied by 0.5 to obtain another part of the corrected frequency image data HIGH'm2(u,v) (step S20). The other (non-selected) frequency image data HIGH(u,v) are used as they are, that is, these non-selected frequency image data are not subjected to no treatment. Accordingly, the corrected frequency image data HIGH'(u,v) (step S10) comprises HIGH'm1(u,v) and HIGH'm2(u,v) and the non-treated HIGH(u,v). These corrected frequency image data HIGH'(u,v) are input to the composite circuit 6 together with the low frequency image data LOW(u,v), and combined with one another to obtain the whole corrected frequency image data F'(u,v).

The above description is made representatively in a case of reading a monochromatic image, however, this invention may be applied in a case of reading a color image as follows.

Figure 5:
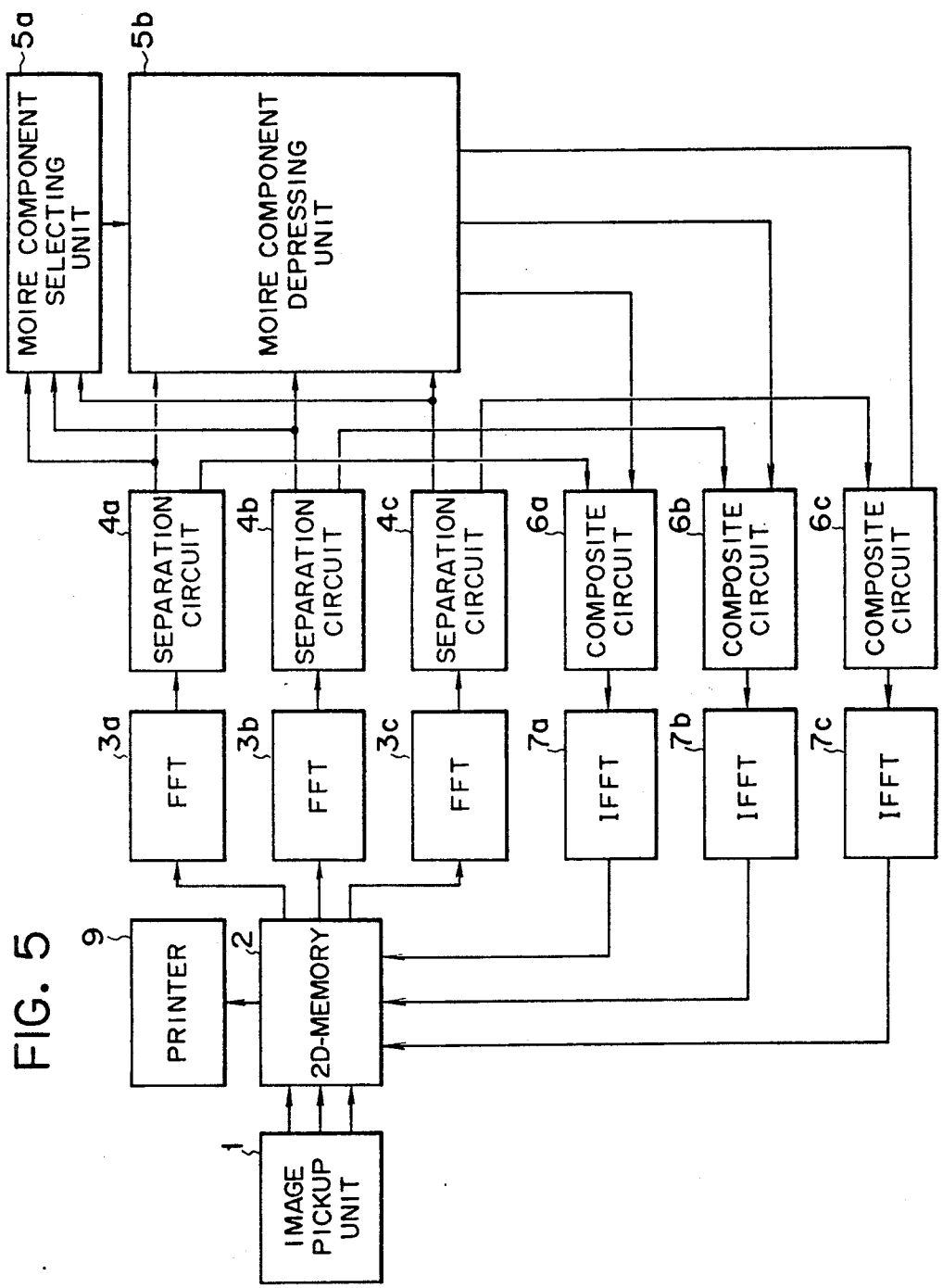
FIG. 5 is a block diagram for showing a second embodiment of the image reading device according to this invention.

FIG. 5 is a block diagram for a second embodiment of the image reading device according to this invention, in which a color original image is read. The construction of the image reading device and the moire component selecting and depressing operations are substantially similar to those of the first embodiment, and the same elements as those of the first embodiment are represented by the same reference numerals.

In this embodiment, an original color image is picked up as red, green and blue color image signals by the image pickup unit 1. Like the first embodiment, each of the red, green and blue color image signals is stored as positional image data in a memory 2'. The stored red, green and blue color image signals are subjected to the fast Fourier transform by FFTs 3a, 3b and 3c for the red, green and blue color image signals, respectively to convert the two-dimensional positional image data of each color image signal into the corresponding two-dimensional discrete spatial frequency image data, and then outputted to separation (frequency separation) circuits 4a, 4b and 4c. In each of the separation circuits 4a, 4b and 4c, the spatial frequency image data are separated into two types of image signals at high frequency coordinate values and low frequency coordinate values (hereinafter referred to as "high frequency image data" and "low frequency image data", respectively) before correcting the moire components (signals). The high frequency image data are inputted to the moire component selecting unit 5a in which the high frequency coordinate values of the moire components are selected, and then the moire components are depressed in the moire component depressing unit 5b. The low frequency image data and the high frequency image data corrected in the moire component selecting and depressing units 5a and 5b for each color image data are inputted to each of the frequency composite circuits 6a, 6b and 6c for each color image data, and the combined frequency image data for each color image date is subjected to the inverse fast Fourier transform by one of IFFTs 7a, 7b and 7c for the respective color image data to reconvert the frequency image data in the spatial frequency coordinate system into the positional image data in the positional coordinate system. The positional image data of each color image data outputted from each of the IFFTs 7a, 7b and 7b are inputted to the two-dimensional memory 2' and then outputted to the printer 9 or the like.

Figure 6:
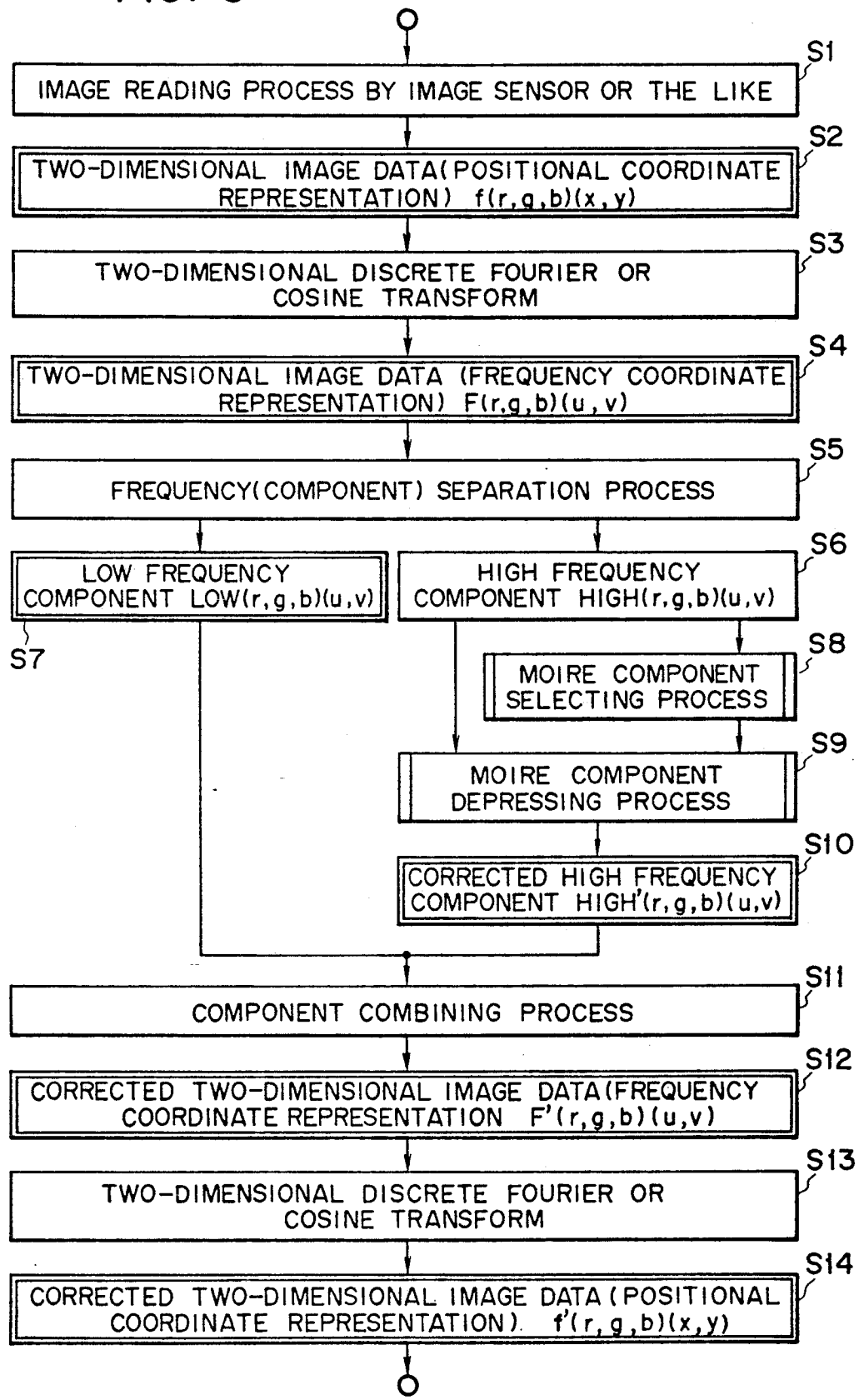
FIG. 6 is a flow chart for showing an image data correcting process of the image reading device as shown in FIG. 5.

FIG. 6 is a flow chart for showing an image data correcting process according to the second embodiment. This process of this embodiment is substantially the same as that of FIG. 2 except that the image data to be subjected to this process comprises three color image data, that is, red, green and blue image data. These color image data are individually and independently subjected to this process by the respective elements as shown in FIG. 5.

The original image is picked up as red, green and blue image signals by the image pickup unit 1 such an image sensor (step S1), and stored as two-dimensional positional image data in the memory 2'. A positional image data at each positional coordinate value (x,y) is represented by one of red, green and blue components fr(x,y), fg(x,y) and fb(x,y) (Step S2), where the red, green and blue components are hereinafter represented by fi(x,y), i=r,g,b.

Next, these color image data are individually subjected to the two-dimensional discrete Fourier transform (or two-dimensional discrete cosine trash) in the FFTs 3a, 3b and 3c, respectively, thereby to convert the two-dimensional positional image data for each color image into the two-dimensional frequency image data for each color image. That is, the positional image data fi(x,y) which is a function of positional coordinate values is converted into the frequency image data Fi(u,v) which is a function of frequency coordinate values (u,v) (step S4).

In the separation circuits 4a, 4b and 4c, the frequency image data for each color image data obtained in the step S3, like the first embodiment, are filtered to separate low frequency components from high frequency components (in a step S5). For example, in a case where the maximum values of the positional coordinate values (x,y) are 256 and 256, respectively, the low frequency components whose frequency range satisfies the following inequality, are separated by a suitable filtering process.

$$-60 < u < 60 \text{ and } -60 < v < 60$$

The low frequency components (image data) Lowe-(u,v) (i=r,g,b) separated in the step S5 are directly subjected to the composite process (step S11) and then used as low frequency components of the corrected two-dimensional frequency image data (step S12). On the other hand, the high frequency components (image data) HIGHi(u,v) separated in the step S5 are subjected to the moire component selecting process (step S8) to extract suitable frequency components (u,v), and then the extracted frequency components are subjected to the moire component depressing process (step S9) to correct the high frequency image data and obtain the corrected high frequency image data HIGH'i(u,v) (step S10).

The low frequency image data LOWi(u,v) and the corrected high frequency image data HIGH'i(u,v) are combined with each other to obtain the corrected two-dimensional image data F'i(u,v) every color image (step S12). That is, three pairs of LOWr(u,v) and HIGH'r(u,v), LOWg(u,v) and HiGH'g(u,v) and LOWb(u,v) and HIGH'b(u,v) are individually combined. The corrected two-dimensional image data F'i(u,v) for each color image data is subjected to the inverse Fourier transform in one of the IFFTs 7a, 7b or 7c to reconvert the two-dimensional frequency image data into the two-dimensional positional image data (step S13), thereby obtaining two-dimensional image data f'i(x,y) (i=r,g,b) whose moire is depressed (step S14).

The moire component selecting and depressing processes of this embodiment are identical to those of the first embodiment as shown in FIG. 3 and 4 except that the image data to be subjected to these processes comprise red, green and blue color image data. These color image data are individually subjected to these processes pursuant to the flow charts as shown in FIG. 3 and 4, and thus the description of these processes of this embodiment is eliminated.

The two-dimensional image data thus corrected for each color image data is stored in the memory 2' and then outputted to the printer 9 or the like.

In this embodiment, the red, green and blue image data may be successively or parallel subjected to the image data correcting process. When the successive correcting process is adopted for the color image data, any order for conducting the correcting process on all the color image data is possible.

In the first and second embodiments, two groups of the frequency coordinate values (first and second moire groups) are used to reduce the moire components. However, another group may be used in the moire component selecting process in addition to the first and second groups. For example, other frequency coordinate values in the neighborhood of the first moire group may be used as a third moire group.

Further, in the above embodiments, the moire components are automatically selected in the moire component selecting process, and thus an user can not freely select the moire components. The following embodiment enable the user to freely select the moire components.

Figure 7:
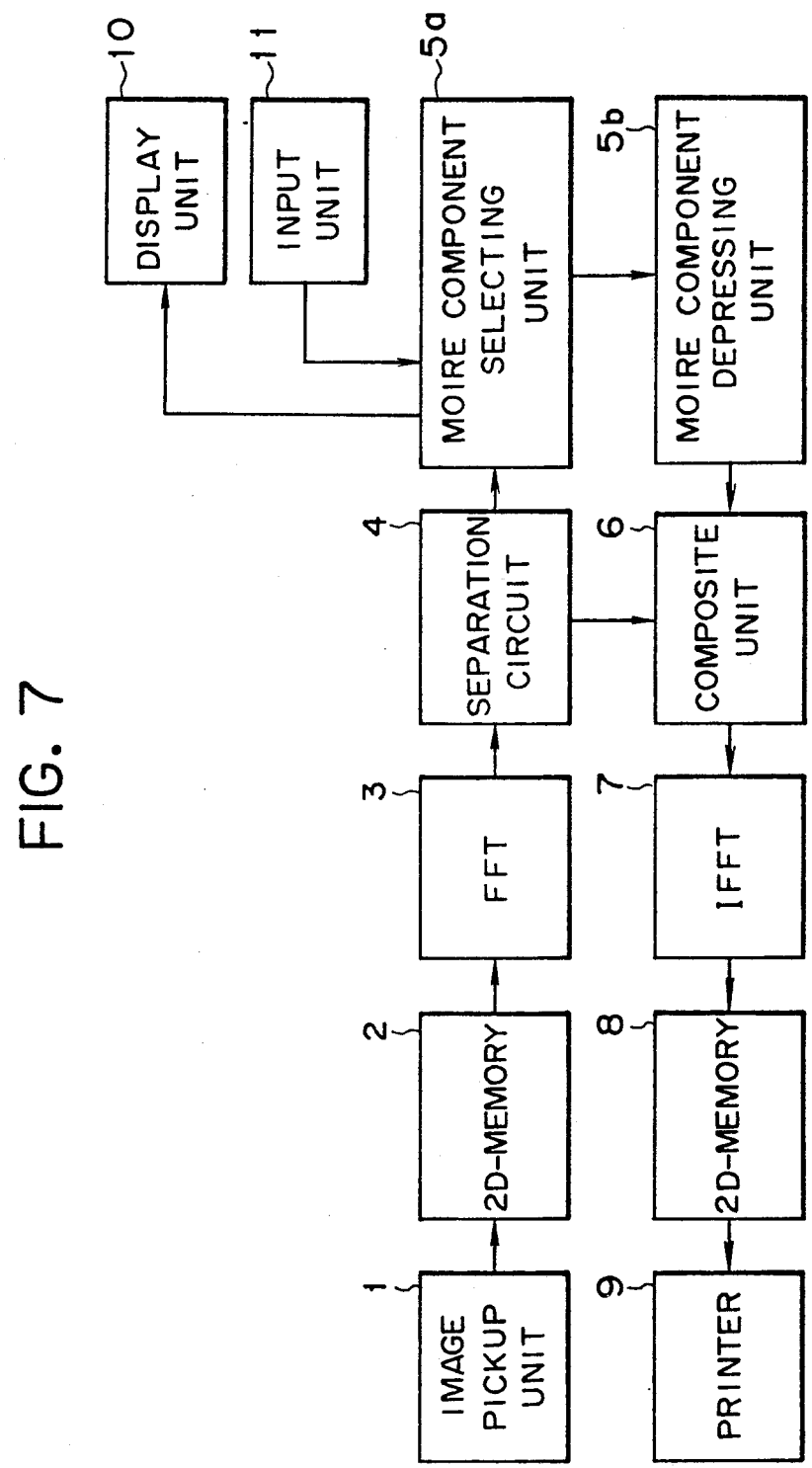
FIG. 7 is a block diagram for showing a third embodiment of the image reading device according to this invention.

FIG. 7 is a block diagram for a third embodiment of the image reading device according to this invention. The image reading device of this embodiment is substantially the same as that of FIG. 1 except that a display unit 10 and an input unit 11 are further provided.

In this embodiment, the moire component selecting unit 5a is connected to the display unit 10 such as a CRT and the input unit 11. The moire component selecting unit supplies the display unit 10 with those frequency coordinate values whose image signals satisfies a condition as described later together with the image signals, and the display unit 10 displays the input frequency coordinate values and the image signals. An user selects those coordinate values whose signals are judged on the basis of the displayed information to be moire components, and inputs the selected moire coordinate values to the moire component selecting unit 5a through the input unit 11.

Figure 8:
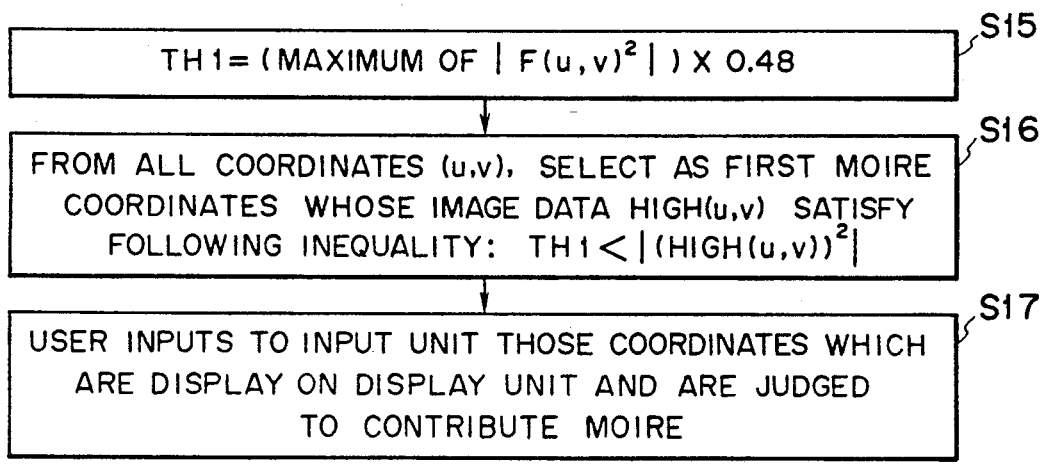
FIG. 8 is a flow chart for showing a moire component selecting process of the image reading device as shown in FIG. 7.

FIG. 8 is a flow chart for showing the moire component selecting process by the user.

In this embodiment, the first threshold level TH1 is set to a value obtained by multiplying the maximum value of absolute values of the second power of frequency image data F(u,v) with 0.48 by a rule of thumb (step S15). As shown in FIG. 8, all of the frequency image data H(u,v) are compared with the first threshold level TH1, and those frequency coordinate values (u,v) whose image data HIGH(u,v) are larger than the first threshold level TH1 ($|HIGH(u,v)^2|max \times 0.48$) are selected and displayed on the display unit 10 together with the image data of these selected frequency coordinate values (step S16). The user selects from the displayed frequency coordinate values moire coordinate values whose image data are judged to be moire components (step S17). On the basis of the selecting operation, one or plural coordinate values which are judged to be moire coordinate values (u1,v1) are input to the moire component selecting unit 5a through the input unit 11, and the frequency image data of the moire coordinate values are successively subjected to the moire component depressing process.

Figure 9:
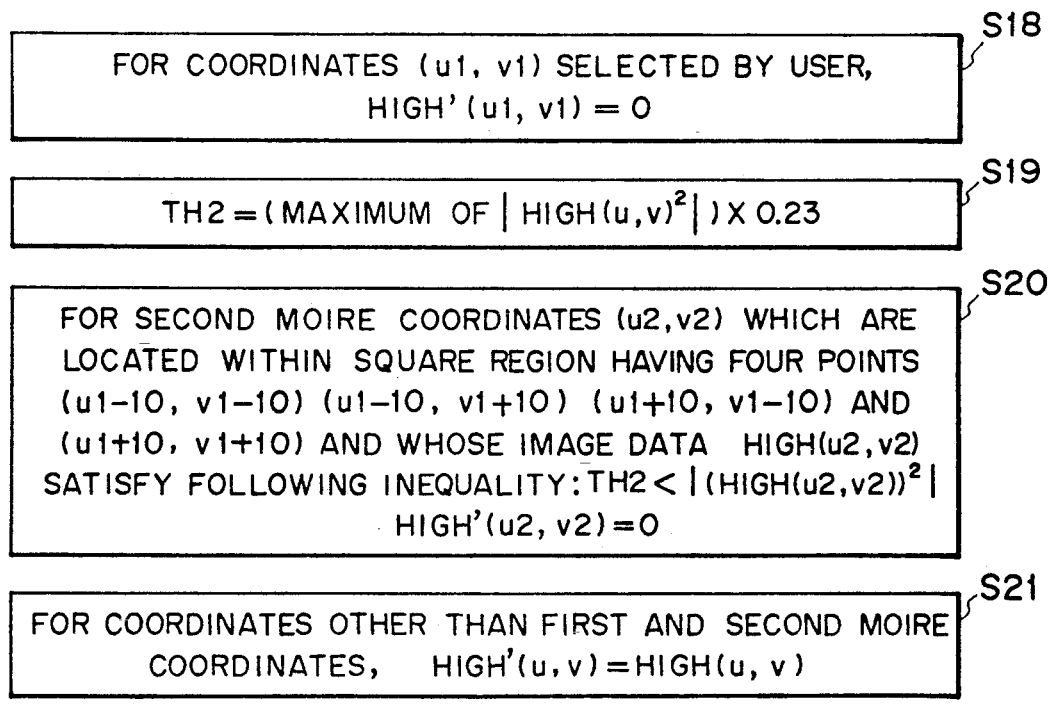
FIG. 9 is a flow chart for showing a moire component depressing process of the image reading device as shown in FIG. 7.

FIG. 9 is a flow chart for showing the moire component depressing process.

In this moire component depressing process, the moire components HIGH(u1,v1) at the selected moire coordinate values (u1,v1) are set to zero (step S18). Further, the second threshold level TH2 is set to a value obtained by multiplying the maximum value of $|HIGH(u,v)^2|$ with 0.23 by a rule of thumb (step S19). In this case, those coordinate values (u,v) which are located within a square region having four points (u1−10, v1−10), (u1−10,v1+10), (u1+10,v1−10) and (u1+10,v1+10) and whose image data HIGH(u,v) satisfy the following inequality are selected as the second moire coordinate values (u2,v2), and the image data HIGH(u2,v2) at those second moire coordinate values (u2,v2) are set to zero (S20). Further, the high frequency image data HIGH(u,v) which are not selected in the steps S18 and S20 are input as corrected image data to the composite circuit 6 with no treatment.

The first and second threshold levels TH1 and TH2 are not limited to the above values, and any values may be freely adopted by the user. For example, these threshold levels may be those of the first embodiment. That is, the first threshold level TH1 may be one-tenth of the absolute value of the second power of F(0,0), and the second threshold level TH2 may be the half of the first threshold level TH1, like the first embodiment. Further, in the above embodiments, a frequency transforming operation such as the fast Fourier or cosine transform is adopted in the transforming process for converting the two-dimensional positional image data into the two-dimensional spatial frequency image data. However, the transforming operation is not limited to the above transforming operations, and any transforming operation (non-positional transforming operation) such as a transforming operation of converting the position image data into autocoorelation image data represented in a two-dimensional discrete correlation coordinate system may be used.

As described above, according to the image reading device of this invention, the pick-up original image data is converted from positional image data into frequency image data through the Fourier transform or the like, and then high frequency components of the frequency image data which are larger than predetermined values (which are judged to be moire components) are selectively reduced, to thereby depressing the moire from an output image. Accordingly, unlike a conventional image reading device using a low path filter, the moire can be depressed without reducing resolution and blurring an output image, and thus an image having no moire can be reproduced even when a dot-printed original image is picked up.

What is claimed is:

1. An image reading device for reading an original image, comprising:
   image pickup means for optically picking up the original image and electrically converting into two-dimensional positional image data represented in a two-dimensional positional coordinate system;

transforming means for converting the two-dimensional positional image data into two-dimensional spatial frequency image data represented in a two-dimensional spatial frequency coordinate system;

separating means for separating the two-dimensional spatial frequency image data into high frequency image data and low frequency image data;

image data correcting means for depressing moire components of the high frequency image data to correct the high frequency image data;

composite means for combining the low frequency image data and the corrected high frequency image data to thereby obtain the corrected two-dimensional frequency image data;

retransforming means for reconverting the corrected two-dimensional frequency image data into corrected two-dimensional positional image data; and outputting means for outputting the corrected two-dimensional positional image data to reproduce the original image with depressing moire.

2. An image reading device as claimed in claim 1, wherein said transforming means comprises a fast Fourier transformer for conducting a two-dimensional discrete Fourier transform on the two-dimensional positional image data, and said retransforming means comprises an inverse fast Fourier transformer for conducting a two-dimensional discrete inverse Fourier transform on the corrected two dimensional frequency image data.

3. An image reading device as claimed in claim 1, wherein said image data correcting means comprises moire component selecting means for selecting from the frequency coordinate values of the input high frequency image data first and second groups of frequency coordinate values whose image data are larger than first and second threshold levels TH1 and TH2, respectively, and moire component depressing means for setting the image data of the first and second groups to first and second predetermined values to thereby depress moire components.

4. An image reading device as claimed in claim 3, wherein the first group comprises frequency coordinate values of the image data HIGH(u,v) satisfying the following inequality: $TH1 < |HIGH(u,v)^2|$.

5. An image reading device as claimed in claim 4, wherein the second group comprises frequency coordinate values of the image data HIGH(nu,nv) satisfying the following inequality: $TH2 < |HIGH(nu,nv)^2|$, wherein n is an integer.

6. An image reading device as claimed in claim 5, wherein the first predetermined value is set to zero.

7. An image reading device as claimed in claim 5, wherein the second predetermined value is set to a value obtained by multiplying each of the image data of the second group by 0.4.

8. An image reading device as claimed in claim 5, wherein the second predetermined value is set to zero.

9. An image reading device as claimed in claim 1, further comprising manual selecting means, connected to said moire component selecting means, for manually determing the moire components on the basis of the high frequency image data from said separating means.

10. An image reading device as claimed in claim 9, wherein said manual selecting means comprises a display unit for displaying the high frequency image data together with frequency coordinate values and an input unit for manually selecting the moire components from the high frequency image data and inputting the moire components to said imag data correcting means.

11. An imag reading device as claimed in claim 1, wherein the original image comprises a color image.

* * * * *